United States Patent
McDevitt et al.

(10) Patent No.: US 11,287,432 B2
(45) Date of Patent: Mar. 29, 2022

(54) SYSTEM AND METHOD FOR DETECTION OF TRAUMA

(71) Applicant: NEW YORK UNIVERSITY, New York, NY (US)

(72) Inventors: John T. McDevitt, New York, NY (US); Deniz Vurmaz, New York, NY (US); Charles DiMaggio, North Merrick, NY (US); Spiros Frangos, New York, NY (US); Marko Bukur, Tenafly, NJ (US); Michael J. Klein, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 16/432,311

(22) Filed: Jun. 5, 2019

(65) Prior Publication Data
US 2019/0369121 A1 Dec. 5, 2019

Related U.S. Application Data

(60) Provisional application No. 62/680,712, filed on Jun. 5, 2018.

(51) Int. Cl.
| | |
|---|---|
| *G01N 33/68* | (2006.01) |
| *B01L 3/00* | (2006.01) |
| *G01N 33/548* | (2006.01) |

(52) U.S. Cl.
CPC ........ *G01N 33/6893* (2013.01); *B01L 3/5027* (2013.01); *G01N 33/548* (2013.01); *B01L 2300/0663* (2013.01); *B01L 2300/0819* (2013.01); *G01N 2333/4704* (2013.01); *G01N 2333/4712* (2013.01); *G01N 2333/4716* (2013.01); *G01N 2333/4737* (2013.01); *G01N 2333/585* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 2012/0322682 A1* | 12/2012 | McDevitt | G01N 33/54313 506/9 |
| 2013/0143243 A1* | 6/2013 | Kobayashi | G01N 33/86 435/7.92 |
| 2014/0094391 A1* | 4/2014 | McDevitt | A61B 10/0051 506/18 |
| 2014/0342381 A1* | 11/2014 | Hayes | G01N 33/54366 435/7.94 |

OTHER PUBLICATIONS

Aoki, M., Hagiwara, S., Tokue, H., Shibuya, K., Kaneko, M., Murata, M., . . . Oshima, K. (2016). Prediction of extravasation in pelvic fracture using coagulation biomarkers. Injury, 47(8), 1702-1706. https://doi.org/10.1016/j.injury.2016.05.012.

(Continued)

*Primary Examiner* — Melanie Brown
(74) *Attorney, Agent, or Firm* — Riverside Law LLP

(57) ABSTRACT

This disclosure describes portable bio-nano-chip assays, methods and compositions for diagnosing trauma at point-of-care using biological samples. The assays, methods and compositions provide in a more convenient, less expensive, and less time-consuming sampling and analysis.

11 Claims, 3 Drawing Sheets

(56) References Cited

OTHER PUBLICATIONS

Brohi, K., Cohen, M. J., Ganter, M. T., Matthay, M. A., MacKersie, R. C., & Pittet, J. F. (2007). Acute traumatic coagulopathy: Initiated by hypoperfusion: Modulated through the protein C pathway? Annals of Surgery, 245(5), 812-818. https://doi.org/10.1097/01.sla.0000256862.79374.31.

Christodoulides, N., Tran, M., Floriano, P. N., Rodriguez, M., Goodey, A., Ali, M., . . . McDevitt, J. T. (2002). A microchip-based multianalyte assay system for the assessment of cardiac risk. Analytical Chemistry, 74(13), 3030-3036. https://doi.org/10.1021/ac011150a.

Dunham, C. M., Frankenfield, D., Belzberg, H., Wiles, C. E. 3rd, Cushing, B., & Grant, Z. (1994). Inflammatory markers: superior predictors of adverse outcome in blunt trauma patients? Critical Care Medicine, 22(4), 667-672.

Fakhry, S. M., Brownstein, M., Watts, D. D., & Baker, C. C. (2000). Relatively Short Diagnostic Delays ( < 8 Hours ) Produce Morbidity and Mortality in Blunt Small Bowel Injury?: An Analysis of Time to Operative Intervention in 198 Patients from a Multicenter Experience. Journal of Trauma-Injury, Infection and Critical Care, 48(3), 408-415.

Floriano, P. N., Christodoulides, N., Miller, C. S., Ebersole, J. L., Spertus, J., Rose, B. G., . . . McDevitt, J. T. (2009). Use of saliva-based nano-biochip tests for acute myocardial infarction at the point of care: A feasibility study. Clinical Chemistry, 55(8), 1530-1538. https://doi.org/10.1373/clinchem.2008.117713.

Ganter, M. T. Brohi, K., Cohen, M. J., Shaffer, L. A., Walsh, M. C., Stahl, G. L., & Pittet, J. F. (2007). Role of the alternative pathway in the early complement activation following major trauma. Shock, 28(1), 29-34. https://doi.org/10.1097/shk.0b013e3180342439.

Gebhard Florian; Nüssler, Andreas K.; Rösen, Margrit; Pfetsch, Helga; Kinzl, Lothar; Bruckner, U. B. (1998). Early posttraumatic increase in production of nitric oxide in humans. Shock, 10(4), 231-236.

Goodey, A., Lavigne, J. J., Savoy, S. M., Rodriguez, M. D., Curey, T., Tsao, A., . . . McDevitt, J. T. (2001). Development of multianalyte sensor arrays composed of chemically derivatized polymeric microspheres localized in micromachined cavities. Journal of the American Chemical Society, 123(11), 2559-2570. https://doi.org/10.1021/ja003341l.

Haase, M., Bellomo, R., Devarajan, P., Schlattmann, P., Haase-Fielitz, A., Bagshaw, S. M., . . . Zhaohui, N. (2009). Accuracy of Neutrophil Gelatinase-Associated Lipocalin (NGAL) in Diagnosis and Prognosis in Acute Kidney Injury: A Systematic Review and Meta-analysis. American Journal of Kidney Diseases, 54(6), 1012-1024. https://doi.org/10.1053/j.ajkd.2009.07.020.

Hagiwara, S., Oshima, K., Aoki, M., Murata, M., Ishihara, K., Kaneko, M., . . . Tamura, J. (2013). Usefulness of fibrin degradation products and d-dimer levels as biomarkers that reflect the severity of trauma. Journal of Trauma and Acute Care Surgery, 74(5), 1275-1278. https://doi.org/10.1097/TA.0b013e31828cc967.

Hanley, A. J., & McNeil, J. B. (1982). The Meaning and Use of the Area under a Receiver Operating Characteristic (ROC) Curve. Radiology, 143, 29-36. https://doi.org/10.1148/radiology.143.1.7063747.

Hirsch, R., Dent, C., Pfriem, H., Allen, J., Iii, R. H. B. Ma, Q., . . . Mitsnefes, M. (2007). NGAL is an early predictive biomarker of contrast-induced nephropathy in children. Pediatric Nephrology, (22), 2089-2095. https://doi.org/10.1007/s00467-007-0601-4.

Huerta-Alardín, A. L., Varon, J., & Marik, P. E. (2005). Bench-to-bedside review: Rhabdomyolysis—An overview for clinicians. Critical Care, 9(2), 158-169. https://doi.org/10.1186/cc2978.

Jokerst, J. V., Jacobson, J. W., Bhagwandin, B. D., Floriano, P. N., Christodoulides, N., & McDevitt, J. T. (2010). Programmable nano-bio-chip sensors: Analytical meets clinical. Analytical Chemistry, 82(5), 1571-1579. https://doi.org/10.1021/ac901743u.

Karabulut, K., Gül, M., Dündar, Z. D., Gander, B., Kurban, S., & Toy, H. (2011). Diagnostic and prognostic value of procalcitonin and phosphorus in acute mesenteric ischemia. Turkish Journal of Trauma & Emergency Surgery, 17(3), 193-198.

Kashuk, J. L., Moore, E. E., Sawyer, M., Wohlauer, M., Pezold, M., Barnett, C., . . . Sauaia, A. (2010). Primary fibrinolysis is integral in the pathogenesis of the acute coagulopathy of Trauma. Annals of Surgery, 252(3), 434-442. https://doi.org/10.1097/SLA.0b013e3181f09191.

Khan, F. Y. (2009). Rhabdomyolysis: a review of the literature. Neth J Med, 67(9), 272-283.

Lane, B. R. (2013). Molecular markers of kidney injury. Urologic Oncology: Seminars and Original Investigations, 31(5), 682-685. https://doi.org/10.1016/j.urolonc.2011.05.007.

Lavigne, J. J., Savoy, S., Clevenger, M. B., Ritchie, J. E., McDoniel, B., Yoo S.-, J., . . . Neikirk, D. (1998). Solution-based analysis of multiple analytes by a sensor array: Toward the development of an "electronic tongue" [15]. Journal of the American Chemical Society, https://doi.org/10.1021/ja9743405, 2 pages.

Mak, T. W., & Saunders, M. E. (2006). Complement. In The Immune Response (pp. 553-581). Elsevier. https://doi.org/10.1016/B978-012088451-3.50021-1.

Malhotra, A. K., Fabian, T. C., Katsis, S. B., Gavant, M. L., & Croce, M. A. (2000). Blunt bowel and mesenteric injuries: The role of screening computed tomography. Journal of Trauma—Injury, Infection and Critical Care, 48(6), 991-1000. https://doi.org/10.1097/00005373-200006000-00001.

Markogiannakis, H., Memos, N., Messaris, E., Dardamanis, D., Larentzakis, A., Papanikolaou, D., . . . Manouras, A. (2011). Predictive value of procalcitonin for bowel ischemia and necrosis in bowel obstruction. Surgery, 149(3), 394-403. https://doi.org/10.1016/j.surg.2010.08.007.

Maves, K. K., & Weiler, J. M. (1993). Properdin: approaching four decades of research. Immunologic Research, 12(3), 233-243.

Mishra, J., Dent, C., Tarabishi, R., Mitsnefes, M. M., Kelly, C., Ruff, S. M., . . . Devarajan, P. (2005). Neutrophil gelatinase-associated lipocalin (NGAL) as a biomarker for acute renal injury after cardiac surgery. The Lancet, 365(9466), 1231-1238.

Mistral, T., Brenckmann, V., Sanders, L., Bosson, J. L., Ferretti, G., Thony, F., . . . Bouzat, P. (2017). Clinical judgment is not reliable for reducing whole-body computed tomography scanning after isolated high-energy blunt trauma. Anesthesiology, 126(6), 1116-1124. https://doi.org/10.1097/ALN.0000000000001617.

Pelsers, M. M. A. L., Hermens, W. T., & Glatz, J. F. C. (2005). Fatty acid-binding proteins as plasma markers of tissue injury. Clinica Chimica Acta, 352(1-2), 15-35. https://doi.org/10.1016/J.CCCN.2004.09.001.

Poletti, P. A., Mirvis, S. E., Shanmuganathan, K., Takada, T., Killeen, K. L., Perlmutter, D., . . . Mermillod, B. (2004). Blunt abdominal trauma patients: Can organ injury be excluded without performing computed tomography? Journal of Trauma—Injury, Infection and Critical Care, 57(5), 1072-1081. https://doi.org/10.1097/01.TA.0000092680.73274.E1.

Relja, B., Szermutzky, M., Henrich, D., Maier, M., De Haan, J. J., Lubbers, T., . . . Marzi, I. (2010). Intestinal-FABP and liver-FABP: Novel markers for severe abdominal injury. Academic Emergency Medicine, 17(7), 729-735. https://doi.org/10.1111/j.1553-2712.2010.00792.x.

Sawamura, A., Hayakawa, M., Gando, S., Kubota, N., Sugano, M., Wada, T., & Katabami, K. ichi. (2009). Disseminated intravascular coagulation with a fibrinolytic phenotype at an early phase of trauma predicts mortality. Thrombosis Research, 124(5), 608-613. https://doi.org/10.1016/j.thromres.2009.06.034.

Szebeni, J., Baranyi, L., Savay, S., Götze, O., Alving, C. R., Bünger, R., & Mongan, P. D. (2003). Complement activation during hemorrhagic shock and resuscitation in swine. Shock (Augusta, Ga.), 20(4), 347-355. https://doi.org/10.1097/01.shk.0000082444.66379.17.

Truedsson, L., Sturfelt, G., Offenbartl, K., & Sjöholm, A. G. (1990). The spleen is not a major synthetic site of alternative pathway components. Complement Inflamm, 7, 52-56.

Tsung, A., Sahai, R., Tanaka, H., Nakao, A., Fink, M. P., Lotze, M. T., . . . Billiar, T. R. (2005). The nuclear factor HMGB1 mediates

(56) References Cited

OTHER PUBLICATIONS hepatic injury after murine liver ischemia-reperfusion. The Journal of Experimental Medicine, 201(7), 1135-1143. https://doi.org/10.1084/jem.20042614.

Weigum, S. E., Floriano, P. N., Redding, S. W, Yeh, C. K., Westbrook, S. D., McGuff, H. S., . . . McDevitt, J. T. (2010). Nano-Bio-Chip sensor platform for examination of oral exfoliative cytology. Cancer Prevention Research, 3(4), 518-528. https://doi.org/10.1158/1940-6207.CAPR-09-0139.

* cited by examiner

SYSTEM AND METHOD FOR DETECTION OF TRAUMA

CROSS-REFERENCE TO RELATED APPLICATIONS

This application claims priority to US provisional patent application No. 62/680,712, filed on Jun. 5, 2018, incorporated herein by reference in its entirety.

BACKGROUND OF THE INVENTION

The need for rapid identification of organ injury and hemorrhage including the early determination of severity in polytrauma is critical to implement immediate and effective medical treatments. The rapid and accurate detection of pertinent biomarkers to assist in early organ injury and hemorrhage identification allows for comprehensive specialized treatments of the injured victim ideally within an hour of the incident. Rapid diagnostics followed by the appropriate therapies are a significant driver of health care costs. In fact, in the United States, approximately 35 million people are treated every year for trauma injuries which includes one hospitalization every 15 minutes. At an annual cost of $67.3B, trauma is the $3^{rd}$ most costly medical condition behind heart disease ($90.9B) and cancer ($71.4B). Yet, a highly effective, comprehensive point-of-care diagnostic device with analysis capabilities facilitating treatments of trauma patients has been elusive.

Organ-specific biomarkers are typically present at their highest concentration in the affected organ and are released into the circulation following injury where they may be measured. At the current time, the bowel, kidney, and spleen do not have true direct organ-specific biomarkers following mechanical injury (unlike the liver and pancreas). Optimized trauma diagnostic panels (such as the one herein envisioned) for use in the immediate post-injury setting (i.e. initial blood draw on patient arrival to hospital) will improve clinical practice by limiting the use of standard computed tomography (CT) imaging modalities. A trauma chip that can reliably rule out an injury to major abdominal viscera may avoid CT entirely, improve trauma care and triage in resource-poor regions, reduce cost of expensive imaging studies, reduce radiation exposure at the population level, and avoid hospital admission in certain circumstances.

Currently, the diagnosis of hollow viscus injury secondary to blunt trauma remains one of the most diagnostically challenging undertakings in trauma surgery and emergency medicine. The accuracy and reliability of diagnosis is lowered by confounders such as large body habitus, the need for repeated evaluations by the same examiner, concomitant neurologic injury, or altered mental status (Fakhry, Brownstein, Watts, & Baker, 2000; Malhotra, Fabian, Katsis, Gavant, & Croce, 2000). Additionally, CT, the gold-standard method of diagnosis of visceral injury, can have a false-negative rate of as high as 12% (Malhotra et al., 2000). As it has been shown that a delay of as little as 8 hours can significantly increase mortality for patients with hollow viscus injury, these faults can have serious implications (Fakhry et al., 2000).

There is thus a need in the art for compositions and methods for diagnosing and treating trauma. The present invention addresses this unmet need in the art.

SUMMARY OF THE INVENTION

In one aspect, a testing cartridge comprises a generally flat substrate having thereon individual bead sensors arranged in an array, wherein each said bead sensor is a porous polymeric bead having an antibody or related bioaffinity ligand bound thereto to form a bead sensor, wherein the antibody or related bioaffinity ligand is specific for a trauma biomarker. In one embodiment, the trauma biomarker is selected from the group consisting of C-reactive protein (CRP), myoglobin, Neutrophil Gelatinase-associated Lipocalin (NGAL), Cystatin-C, Kidney Injury Marker 1 (KIM-1), High Mobility Group Box 1 (HMGB-1), Liver Fatty Acid Binding Protein (L-FABP), Intestinal Fatty Acid Binding Protein (I-FABP), procalcitonin, properdin, complement component 5, Fibrin Degradation Products (FDP), and protein C.

In one embodiment, the testing cartridge further comprises internal microfluidics on said substrate for carrying fluid to and from said bead sensors. In one embodiment, the testing cartridge further comprises a sample entry port. In one embodiment, the testing cartridge further comprising at least one reagent blister fluidly connected to said bead sensors. In one embodiment, the testing cartridge further comprises at least one waste fluid chamber fluidly connected to and downstream of said bead sensors. In one embodiment, the testing cartridge further comprises positive and negative control bead sensors and calibrator bead sensors.

In one embodiment, every said bead sensor is present in said array in at least duplicate. In one embodiment, every said bead sensor is present in said array in at least duplicate. In one embodiment, said antibody or bioaffinity ligand is conjugated to said bead sensor via a linker. In one embodiment, said cartridge further comprises a) one or more reagent chambers fluidly connected to and upstream of said array, b) one or more waste fluid chambers fluidly connected to and downstream of said array, c) a sample inlet upstream and fluidly connected to said one or more reagent chambers, and d) wherein each bead sensor is a porous polymeric bead of size between 50-300 μm±10%.

In another aspect, an assay for the diagnosing trauma comprises the steps of obtaining a biological sample from a patient, immunologically testing said sample to determine the level of trauma biomarkers, and wherein said testing is conducted on an array of agarose beads, conjugated to antibodies, and wherein signal from said array of agarose beads is analyzed by circular area of interest or line profiling or both. In one embodiment, the antibody is specific for a biomarker selected from the group consisting of C-reactive protein (CRP), myoglobin, Neutrophil Gelatinase-associated Lipocalin (NGAL), Cystatin-C, Kidney Injury Marker 1 (KIM-1), High Mobility Group Box 1 (HMGB-1), Liver Fatty Acid Binding Protein (L-FABP), Intestinal Fatty Acid Binding Protein (I-FABP), procalcitonin, properdin, complement component 5, Fibrin Degradation Products (FDP), and protein C.

In one embodiment, the trauma is abdomino-pelvic trauma. In one embodiment, the trauma is organ-specific trauma. In one embodiment, the organ-specific trauma is trauma to an organ selected from the group consisting of spleen, liver, intestines, and kidneys. In one embodiment, the trauma is hemorrhage. In one embodiment, the assay diagnoses the severity of the trauma.

In another aspect, a trauma diagnostic system comprises a microfluidic lab-on-chip based immunoassay that comprises a disposable cartridge and a separate reader, wherein said cartridge fits into a slot on said reader, and said reader performs said immunoassay and outputs a result, said cartridge comprising a generally flat substrate having embedded microfluidic channels connecting an inlet port to an embedded downstream assay chamber having a transparent cover and containing a removable array of bead sensors, ii) one or more reagent chambers fluidly connected to and upstream of said assay chamber, and iii) one or more waste fluid chambers fluidly connected to and downstream of said assay chamber; wherein each bead sensor is a porous polymeric bead of size between 50-300 microns±10% having an antibody conjugated thereto, wherein said antibody is specific for a target selected from the group consisting of C-reactive protein (CRP), myoglobin, Neutrophil Gelatinase-associated Lipocalin (NGAL), Cystatin-C, Kidney Injury Marker 1 (KIM-1), High Mobility Group Box 1 (HMGB-1), Liver Fatty Acid Binding Protein (L-FABP), Intestinal Fatty Acid Binding Protein (I-FABP), procalcitonin, properdin, complement component 5, Fibrin Degradation Products (FDP), and protein C.

In another aspect, a kit comprises the cartridge as described above wrapped in an airtight package.

In another aspect, a method for diagnosing or treating trauma comprises obtaining a biological sample from a patient and immunologically testing said sample to determine the level of one or more trauma biomarkers; wherein said testing is conducted on an array of agarose beads. In one embodiment, the biomarker is selected from the group consisting of C-reactive protein (CRP), myoglobin, Neutrophil Gelatinase-associated Lipocalin (NGAL), Cystatin-C, Kidney Injury Marker 1 (KIM-1), High Mobility Group Box 1 (HMGB-1), Liver Fatty Acid Binding Protein (L-FABP), Intestinal Fatty Acid Binding Protein (I-FABP), procalcitonin, properdin, complement component 5, Fibrin Degradation Products (FDP), and protein C.

In one embodiment, the method further comprises performing an interventional radiologic or operative technique. In one embodiment, the method further comprises assigning a risk-stratification to the patient. In one embodiment, the method further comprises performing an optimal clinical intervention, when the level of the one or more biomarkers are above a threshold level. In one embodiment, the optimal clinical intervention is selected from the group consisting of exploratory laparotomy, emergency thoracotomy, resuscitation and chest wall stabilization.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Figure 1:
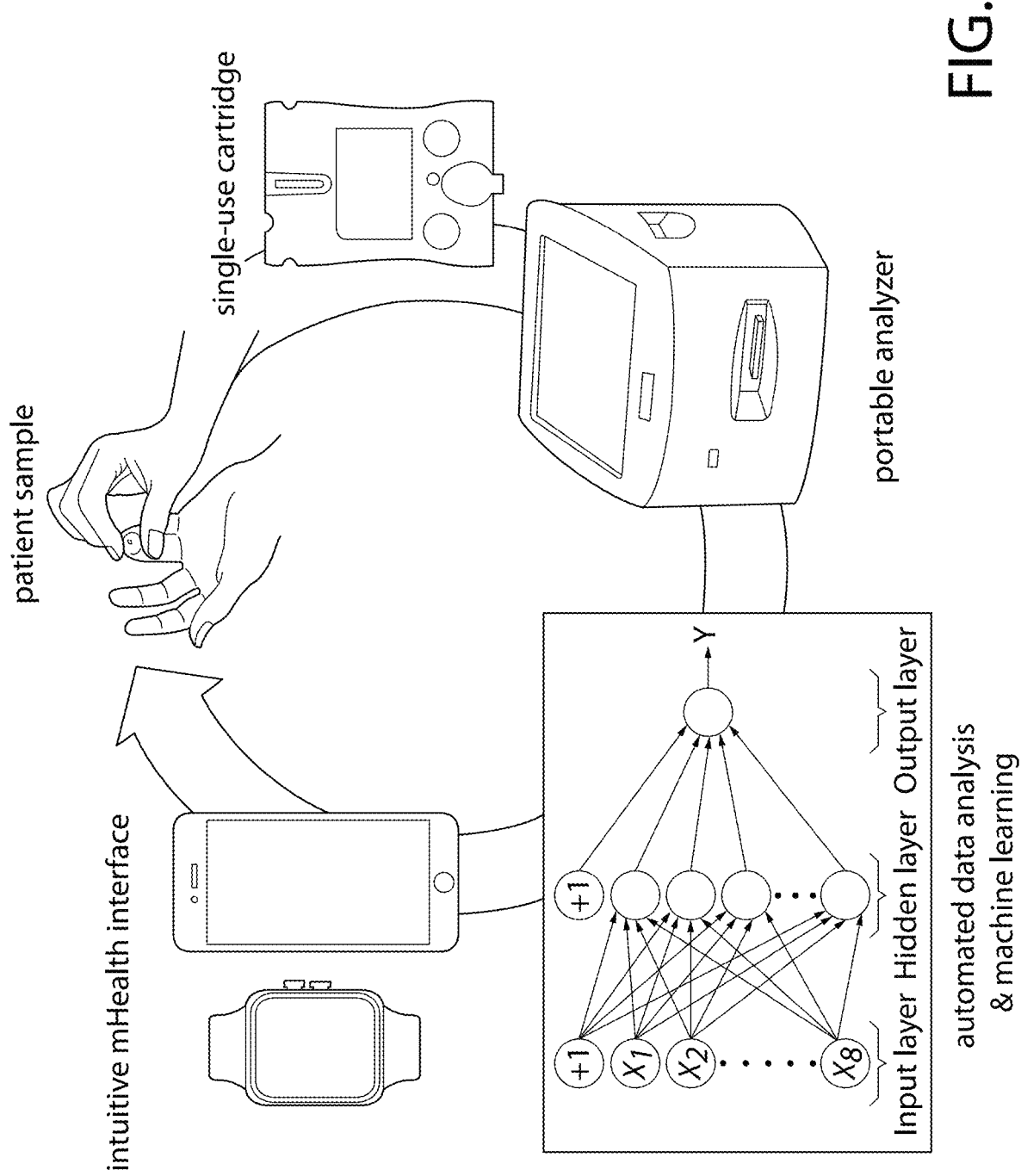
FIG. 1 depicts a schematic of the intended use cycle of the programmable bio-nano-chip (p-BNC) system. This is a flexible platform for digitizing biology, featuring sensor ensembles that measure biomarkers in highly efficient manner.

The invention generally relates to point of care diagnostics for trauma, disposable cassettes or lab cards containing biomarker specific reagents, portable devices for use as analyzers or drivers with same, software to evaluate and report test results, and the overall diagnostics and reporting system as a whole.

In one aspect, the invention provides a programmable bio-nano-chip (p-BNC)-based assay for detecting the concentration of a trauma biomarker in a biological sample. Such a chip can be used with the laboratory based p-BNC instrumentation, the portable p-BNC assay system or a hand-held device designed for point-of care use.

The p-BNC is a packaged microfluidic sample processing and immune-analysis chip that serves as the functional component for the detection and quantitation of the one or more biomarkers.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

By "reader" or "detector" or "analyzer" what is meant is a device that contains the optics, optic sensing means, processor, user interface, and fluidics and is the device that runs the assays described herein and thus "analyzes" the sample and "reads" or "detects" the results.

By "card" or "cartridge" what is meant is a generally planar substrate having microfluidic channels and chambers therein, as well as one or more access ports, and houses the bead array specific for the assays described herein.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

It is understood that in certain embodiments and examples, an antibody as described may be replaced with any bioaffinity ligand. Suitable bioaffinity ligands include any molecule that binds to a biomarker of interest. Exemplary bioaffinity ligands include, but are not limited to, antibodies, antibody fragments, proteins, peptides, peptidomimetics, nucleic acid molecules, bacteriophages, aptamers, and small molecules.

By the term "specifically binds," as used herein with respect to an antibody or bioaffinity ligand, is meant an antibody or bioaffinity ligand which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

As used herein, the term "marker" or "biomarker" is meant to include a parameter which is useful according to this invention for determining the presence and/or severity of trauma.

The term "control or reference standard" describes a material comprising none, or a normal, low, or high level of one of more of the marker (or biomarker) expression products of one or more the markers (or biomarkers) of the invention, such that the control or reference standard may serve as a comparator against which a sample can be compared.

As used herein, an "immunoassay" refers to a biochemical test that measures the presence or concentration of a substance in a sample, such as a biological sample, using the reaction of an antibody to its cognate antigen, for example the specific binding of an antibody to a protein. Both the presence of the antigen or the amount of the antigen present can be measured.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

The "level" of one or more biomarkers means the absolute or relative amount or concentration of the biomarker in the sample.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Sample" or "biological sample" as used herein means a biological material isolated from an individual, including but is not limited to organ, tissue, exosome, breast milk, blood, plasma, saliva, urine and other body fluid. The biological sample may contain any biological material suitable for detecting the desired biomarkers, and may comprise cellular and/or non-cellular material obtained from the individual.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient. The term "microarray" refers broadly to both "DNA microarrays" and "DNA chip(s)," and encompasses all art-recognized solid supports, and all art-recognized methods for affixing nucleic acid molecules thereto or for synthesis of nucleic acids thereon.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to expanded panel of biomarkers to diagnose trauma in a biological sample. In one embodiment, the panel of biomarker reveals organ specific trauma. In one embodiment, the biological sample is analyzed for expression of molecular biomarkers including at least 1, 2, 3, 4, 5, 6, 7, 8, 9, 10, 11 or all of C-reactive protein (CRP), myoglobin, Neutrophil Gelatinase-associated Lipocalin (NGAL), Kidney Injury Marker 1 (KIM-1), High Mobility Group Box 1 (HMGB-1), Liver Fatty Acid Binding Protein (L-FABP), Intestinal Fatty Acid Binding Protein (I-FABP), procalcitonin, properdin, complement component 5, Cystatin-C, Fibrin Degradation Products (FDP), and protein C.

The programmable bio-nano-chip approach is compared to the current standard of care based on incident, medical and surgical history; head-to-toe physical exam; adjunct radiographic imaging (e.g. chest x-ray, pelvis x-ray, FAST exam, angiography, CT and MRI imaging); laboratory evaluation, including blood and urine analysis; surgery (if indicated to treat injury); and angioembolization (if indicated to treat injury).

In some embodiments, the analysis may be performed using a hand-held device with disposable chip that provides a rapid, cost effective, yet sensitive method of detecting these trauma markers. Additionally, because of its portability, low cost, and speed, this approach can function in point of care settings using noninvasive samples, including, but not limited to brush biopsy samples, blood samples, saliva samples, and urine samples. The invention therefore also includes the disposable chip with reagents placed thereon that are specific for measuring the above markers. In some embodiments, the device contains power, detection of signal, programming, and capacity to display the final results.

A trauma chip that can reliably rule out an injury to major abdominal viscera may avoid CT entirely, improve trauma care and triage in resource-poor regions, reduce cost of expensive imaging studies, reduce radiation exposure at the population level, and avoid hospital admission in certain circumstances.

Programable Bio-Nano-Chip

In one aspect, the invention provides a Programable Bio-Nano-Chip (p-BNC) that allows for the analysis of a biological fluid for the diagnosis and management of trauma patients. The p-BNC system allows for the simultaneous quantification of expression of multiple molecular biomarkers of trauma in an automated manner using refined image analysis algorithms based on pattern recognition techniques and advanced statistical methods (see e.g., FIG. 1). In certain embodiments, the device has at least 90% specificity and 90% sensitivity, preferably at least 92, 93, 94, 95, 96, or 97%.

In one embodiment, the invention provides a testing cartridge comprising a generally flat substrate having thereon individual bead sensors arranged in an array, wherein each bead sensor is a porous polymeric bead having at least onebioaffinity ligand bound thereto, wherein said bioaffinity ligand is specific for a target selected from C-reactive protein (CRP), myoglobin, Neutrophil Gelatinase-associated Lipocalin (NGAL), Kidney Injury Marker 1 (KIM-1), High Mobility Group Box 1 (HMGB-1), Liver Fatty Acid Binding Protein (L-FABP), Cystatin-C, Intestinal Fatty Acid Binding Protein (I-FABP), procalcitonin, properdin, complement component 5, Fibrin Degradation Products (FDP), and protein C. Exemplary bioaffinity ligands include, but are not limited to, antibodies, antibody fragments, proteins, peptides, peptidomimetics, nucleic acid molecules, bacteriophages, aptamers, and small molecules.

In one embodiment, the testing cartridge further comprising internal microfluidics on said substrate for carrying fluid to and from said bead sensors. In one embodiment, the testing cartridge further comprises a sample entry port. In one embodiment, the testing cartridge further comprises at least one reagent blister fluidly connected to said bead sensors. In one embodiment, the testing cartridge further comprises at least one waste fluid chamber fluidly connected to and downstream of said bead sensors. In one embodiment, the testing cartridge further comprises positive and negative control bead sensors and calibrator bead sensors having known amounts of a target antigen being calibrated.

In one embodiment, every antigen bead sensor is present in said array in at least duplicate. In one embodiment, every antigen bead sensor is present in said array in at least triplicate. In one embodiment, the antibody is conjugated to said bead sensor via a linker.

In one embodiment, the invention provides a testing cartridge further comprising one or more of the following: one or more reagent chambers fluidly connected to and upstream of said array; one or more waste fluid chambers fluidly connected to and downstream of said array; a sample inlet upstream and fluidly connected to said one or more reagent chambers; and wherein each bead sensor is a porous polymeric bead of size between 50-300 µm±10%.

In one embodiment, the diagnostic is performed on a portable device together with disposable biochips, that contains various liquid and/or dried reagents. The analyzer device contains microfluidics for sample and reagent flow, means for detecting signals, usually light-based signals, computing means for analyzing collected data and usually means for inputting patient information and displaying final results.

In one embodiment, the disposable lab cards or cartridges contain a detection window which has a membrane therein sized to capture cells. In one embodiment, the membrane is exchangeable, e.g., with membranes of differing size, or with arrays of antibodies, and thus is contained inside a hinged door or lid or similar components that serves to lock the exchangeable component into the card.

In certain embodiments, the cartridges can be used to analyze and image whole cells. In one embodiment, an inlet port is fluidly connected to the detection window, and sample is applied and travels to the window where cells are trapped by the membrane. In one embodiment, the cartridge further comprises regent chambers, and the reader activates the reagent chamber, pushing wash fluid to the assay chamber to wash away cell debris as needed. Next, a second reagent chamber is activated, and travels past a dry pad or chamber containing dry bioffinity ligands (e.g. antibodies) and stains, reconstitutes same and carries these to the assay chamber, where the cells are stained with nuclear, cytoplasmic and antibody stains. Optionally, these reagents can be premixed with the second chamber fluid. In one embodiment, the stability of antibody components is improved in the dry form. In one embodiment, the dry pads are exchangeable, e.g. via a hinged lid. The excess reagents can then be washed away, using wash from the first chamber, and the remaining signals detected and analyzed. Additional assay chambers can be provided, depending on the number of analytes to be analyzed and the spectral range of the signals (and device capacity to distinguish same). Alternatively, the cells can be serially stained, and then washed clean and restrained.

Compared to gold standard methods, such as enzyme-linked immunoassay (ELISA), the p-BNC system exhibits assay times in minutes instead of hours, limits of detection (LOD) two or more orders of magnitude lower, and a proven capacity to multiplex 5 or more concurrent analytes with appropriate internal controls and calibrators. For example, salivary biomarkers that were previously undetectable by standard methods, may now be targeted with the portable testing devices to assess systemic disease in a non-invasive fashion. Examples of such devices are set forth in Goodey et al., J. Amer. Chem. Soc., 123(11):2559-2570, 2001, and Christodoulides et al., Lab. Chip, 5(3):261-9, 2005b, the entire contents of which are incorporated by reference into this application.

The strong analytical performance of the p-BNC system may be attributed to the porous nature of its agarose bead sensors, the active transport mode of delivery of the sample and detection reagents, as well as the highly stringent washes associated with this micro-fluidic approach. Like ELISA, the bead-based p-BNCs complete two-site immunometric, as well as competitive, immunoassays; however, unlike ELISA, which limits the diffusion-mediated antigen (Ag)-Antibody (Ab) binding to a 2-dimensional, planar surface at the bottom of the well, the p-BNC cards provide a ~1,000 to 10,000-fold increase in surface area on the 3-dimensional bead or disk sensor. This 3-dimensional reactor allows for significantly increased contact area, as well as on, off and then on again, higher avidity Ag-Ab interactions.

All of the afore-mentioned features contribute to the generation of high signal-to-noise ratios, which ultimately translate into the advanced detection capabilities associated with the p-BNC system.

In one embodiment, the invention is directed to a disposable cartridge, cassette, or lab card, wherein the testing sites comprise agarose substrates (beads or disks) that are conjugated to either target or anti-target antibody, and thus serves in competitive or sandwich two-site immunometric assays. In one embodiment, the agarose substrates are agarose beads. In one embodiment, the agarose substrate is conjugated to an anti-target antibody. In one embodiment, the anti-target antibody is specific for a target selected from CRP, myoglobin, NGAL, Cystatin-C, KIM-1, HMGB-1, L-FABP, I-FABP, procalcitonin, properdin, complement component 5, FDP, and protein C.

The cartridge comprises channels and other microfluidics, such that fluid can be forced to pass through the agarose beads or disk. Blister packs or other chambers can also be placed on the cartridge and can contain, e.g., wash fluids, reagent fluids, and the like. Channels designed for mixing and fluid flow permeate this architecture, and manipulations of the fluidic cartridges reconstitute and disperse reagents through the lab card. Linear actuation controls all fluid motion via pressure actuation steps provided by the analyzer device.

In more detail, a sample entry port is fluidly connected via microfluidics to the assay chamber. In certain embodiments, the assay chamber comprises a plurality of bead sensors as described herein. In certain embodiments, the assay chamber is addressable from the exterior of the cartridge to allow for insertion of an array of bead sensors into the assay chamber; thereby allowing for different arrays of bead sensors (i.e. different arrays specific for different markers and indications) to be swapped in and out of the assay chamber. The assay chamber is either open to the environment or comprises a transparent lid to allow for imaging and image analysis of the cells within assay chamber. In certain embodiments, one or more pinch valves function to allow controlled delivery of microfluidic elements. In some embodiments, buffer entry ports are fluidly connected to microfluidics of the cartridge. In certain embodiments, one the cartridge comprises one or more blister packs that contain liquid reagents, such as wash buffers. Blister packs allow for a self-contained cartridge with a smaller footprint. Alternatively, the device could be connected directly to an external fluid source via buffer entry ports. The blisters are accessed via pressure actuation, a function provided by the analyzer/reader and embedded software, and thus are preferably foil blisters.

In certain embodiments, the cartridge comprises a bubble trap which allows for pressure relief, otherwise the fluid would not flow in the microfluidic channels. Alternatively, waste chambers can be closed under negative pressure and thus pull fluid in their direction when a valve is opened. In one embodiment, the cartridge comprises a reagent port, which can contain an absorbent pad having dried reagents thereon. Thus the reagent port can consist of an access hatch or affixed cover and a recess, into which a reagent pad can be placed. Alternatively, the reagent port could be a blister pack or an inlet allowing connection to external fluids. In certain embodiments, the cartridge comprises a waste reservoir and a waste reservoir external vent fluidly connected via a microfluidic channel to the assay chamber having a transparent access hatch or affixed cover allowing visual access to the chamber. The cartridge may also comprise a port to a waste chamber, although the chamber can be made sufficiently large to hold all waste and this port omitted.

In certain embodiments, the cartridge is a disposable plastic chip made by injection molding and/or etching of parts and adhering layers together. Exemplary materials for constructing the cartridge are plastics of durometer 34-40 Shore D for the substrate and microfluidics, such as polymers and copolymers of styrene, acrylic, carbonate, butadiene, propylene, vinyl, acrylonitrile, and foil for the blisters.

In certain embodiments, the cartridge comprises one or more reagents (e.g. labeled detecting antibodies) for detection of biomarkers. For example, the bead sensor comprises a first antibody to capture a biomarker from the sample, while the cartridge comprises a second antibody (e.g. a labeled detecting antibody) that binds to a different epitope of the marker while bound to the first antibody of the bead sensor. The reagents may be within a blister pack or dried on a reagent pad.

In one embodiment, a reagent chamber is activated, allowing for a fluid or buffer to travel past a dry pad or chamber containing dried reagents (e.g., antibodies and stains), reconstitutes the same and carries these to the assay chamber. Optionally, these reagents can be premixed with the second chamber fluid. In one embodiment, the stability of antibody components is improved in the dry form. In one embodiment, the dry pads are exchangeable, e.g. via a hinged lid. The excess reagents can then be washed away, using wash from the first chamber, and the remaining signals detected and analyzed. In one embodiment, the dried reagents comprise one or more types of bioaffinity ligand. Additional assay chambers can be provided, depending on the number of analytes to be analyzed and the spectral range of the signals (and device capacity to distinguish same).

Further details of the cartridges may be found in U.S. Ser. No. 13/745,740, filed Jan. 18, 2013, Ser. No. 14/025,163, filed Sep. 12, 2013, Ser. No. 14/027,320, filed Sep. 16, 2013, Ser. No. 15/154,100, filed May 13, 2016, Ser. No. 15/658,730, filed Jul. 25, 2017, 61/484,492, filed May 10, 2011, and 61/558,165, filed Nov. 10, 2011, which are all expressly incorporated by reference herein in their entireties.

The cartridges may be constructed from common, inexpensive materials, including vinyl adhesive, laminate, stainless steel, and poly-(methyl methacrylate) (PMMA). Computer-aided design (CAD) models the cartridges, and then a CAD plotter/cutter incises the vinyl. Up to seven layers of vinyl/laminate are deposited on six to eight cartridges using conventional, parallel layering methods. In certain embodiments, cartridges are disposable and purposed to service one patient and a single assay. The cartridges may also be prepared from a three-layer plastic stack prepared by injection molded plastic methods. These three layers are sealed into a single coherent part using laser sealing procedures or various adhesive layers.

The agarose can be plain agarose, or any of the agarose derivatives such as cross-linked agarose, sepharose, or any agarose derivatives that can be used for affinity chromatography. The array can be on agarose beads or disk, as discussed above. Where disks are employed, the disk is preferably about 10-50 μm thick and 50-200 μm in width, but larger or smaller sizes are also possible, depending on sample size, specificity of the reagents, and the sensitivity of the instrumentation.

In one embodiment, the disk sits on a porous support or substrate, and the fluidics are such that fluid is forced through the disk. The porous substrate can be any membrane, such as nitrocellulose membrane, or poly(methyl methacrylate) (PMMA) membrane. It can also be a more substantive support, such as porous glass, ceramic, plastic (delrin, PMMA, acrylonitrile butadiene styrene, i.e. Abs), or metallic (e.g., stainless steel) frit. In one embodiment, the disk can sit in a well, and the fluids merely pass over the disk in the same way they would a bead. Where wells are used, either a plastic, glass, silicon, or stainless-steel chip arrayed with wells, each of which hosts an individual bead or disk sensor, may be used to complete the cartridge.

These arrays of antibodies can be easily exchanged, by substituting a new array on the cartridge, thus quickly and easily reprogramming the card for a new assay. The reprogramming can be completed, by uploading assay specific software to the analyzer device, via e.g., USB, and/or by providing different reagents and fluids in the blister packs or chambers or in dry reagent pads as needed.

In one embodiment, the cartridge comprises a detection or analysis window. In one embodiment, the analysis window can be covered with a transparent cover such as glass, polycarbonate, acrylic, and the like, under which is housed the array of agarose beads or disks. The cover is optional, particularly where the array is added by the user at the time of the test. However, if the array and cartridge are preassembled for sale, a cover can be beneficial as it prevents the array chip containing the agarose beads from getting dehydrated. The capture antibody conjugated beads are prepared in batches and are stored until use, with a demonstrated long-term stability. In one embodiment, a common detector antibody is contained in an upstream chamber in a dry form (e.g., in a dry porous pad) along with excipients to promote long term stability.

In one embodiment, a sample is applied to the cartridge via a specimen entry port, and the sample travels to the detection window where the arrayed capture antibodies capture the analyte of interest. Wash fluid (e.g., PBS or PBS plus detergent) from a blister pack on the cartridge is then activated, and travels to the array to wash away unbound sample. Next, PBS or other appropriate buffer is released and en route to the analysis window collects and reconstitutes the detection antibody, which will then stain the captured analytes on the beads or disks. Additional wash solution follows to wash off unbound detector antibody. A waste chamber downstream of the array collects all waste fluids leaving the array.

In one embodiment, purified calibration standards in the array are first analyzed to derive the standard curves to which tested clinical samples are compared. Dedicated image analysis algorithms convert fluorescent signals from the sample into quantitative measurements, through interpolation of signals developed from testing of samples on a dose curve generated from the purified calibration standards. These values are then used, together with any patient information that was inputted into the device to prepare and report a risk of trauma.

Compared with gold standard systems, such as enzyme-linked immunoassay (ELISA), the p-BNC system has assay times measured in minutes rather than hours, limits of detection (LOD) two or more orders of magnitude lower, and multiplex capacity of 10 or more concurrent analytes with appropriate internal controls.

Biomarkers

In one aspect, the invention provides a systems and method for the diagnosis and management of trauma patients. For example, the system and method described herein can be used to quickly evaluate a subject as having or not having: hemorrhage abdominal trauma, polytrauma, organ-specific trauma (e.g., liver trauma, pancreatic trauma, splenic trauma, bowel trauma, kidney trauma, traumatic brain injury, lung trauma, traumatic pelvic injury etc.), penetrating trauma wound (e.g. stab wound or gunshot wound), non-penetrating trauma or blunt trauma, (head trauma, chest trauma, bone fracture, traumatic traffic or sports injuries, home and industrial accidents, and thermal, electrical, chemical or radioactive exposure), and the like.

In one embodiment, the method comprises determining the level of one or more biomarkers in a biological sample and diagnosing a patient with trauma. In one embodiment, the biomarker is selected from CRP, myoglobin, NGAL, Cystatin-C, KIM-1, HMGB-1, L-FABP, I-FABP, procalcitonin, properdin, complement component 5, FDP, and protein C.

The biomarker C-reactive protein (CRP) is a well-established marker of acute inflammation, and is used to determine the presence or resolution of infections and inflammatory states. Traumatic injury has been shown to be an early upregulator of hepatic synthesis of CRP, with serum levels rising as early as within 6 hours of induced stimulus (Gebhard Florian; Nüssler, Andreas K.; Rösen, Margrit; Pfetsch, Helga; Kinzl, Lothar; Bruckner, 1998). Plasma CRP levels have also been shown to be significantly elevated after both mechanical trauma and burns (Dunham et al., 1994).

Myoglobin (Mb) is found in abundance in human muscle tissue, and is released in response to tissue destruction and ischemia. Although it is a specific marker of muscle injury and appears to be elevated in plasma within 1 hour of injury, it is not typically used in the diagnosis of rhabdomyolysis due to its combination of metabolism to bilirubin and renal excretion, resulting in a half-life of 2-3 hours. This leads to complete clearance within 6-8 hours in the absence of ongoing injury, and sets up a potential for false-negative results and missed diagnoses (Huerta-Alardin, Varon, & Marik, 2005). A more commonly-used marker of rhabdomyolysis and polytrauma is creatine kinase (CK), which demonstrates elevated plasma levels within 2-12 hours of injury and has a half-life of 1.5 days (Khan, 2009). For this reason, it has become the de facto standard for the diagnosis of rhabdomyolysis in many institutions. Due to the more rapid rise of serum myoglobin levels in an acute trauma setting, however, where patients are typically evaluated within 1 hour of injury, detection of elevated Mb may offer earlier diagnosis of significant tissue destruction than elevated CK levels. New opportunities exist when biomarker panels are used and the information on the time course change of the biomarkers may be used to determine severity of trauma complications.

N gelatinase-associated lipocalin (NGAL) may be a potential early marker of ischemia-reperfusion injury in the kidney. Serum NGAL concentrations are dramatically elevated in children who go on to develop AKI, and that these concentrations rise as quickly as 2 hours after insult. Similar to children, most trauma patients are relatively young without chronic comorbidities, making serum NGAL an attractive potential marker for acute traumatic kidney injury. Serum and urine NGAL levels have also been shown to be powerful predictors of the development of contrast nephropathy, which is an important consideration in a blunt trauma population where the large proportion of patients are sent for CT scans with IV contrast (Haase et al., 2009; Hirsch et al., 2007).

Cystatin C is mainly used as a biomarker of kidney function that has a low molecular weight (approximately 13.3 kilodaltons), and it is removed from the bloodstream by glomerular filtration in the kidneys. If kidney function and glomerular filtration rate decline, the blood levels of cystatin C rise. Cross-sectional studies (based on a single point in time) suggest that serum levels of cystatin C are a more precise test of kidney function (as represented by the glomerular filtration rate, GFR) than serum creatinine levels (Dharnidharka, 2007).

High mobility group box 1 (HMGB1) is widely known to be a late mediator of the septic inflammatory response, but has also been shown to be expressed as early as 1 hour after ischemia/reperfusion injury of hepatocytes (Tsung et al., 2005). While serum alanine aminotransferase (ALT) is accepted as a sensitive marker of hepatic injury in trauma, it is a relatively large protein that is slow to show increases in serum levels after cell injury (Pelsers, Hermens, & Glatz, 2005). When sent for analysis, serum ALT also takes approximately 1 hour to result in most institutions (Poletti et al., 2004), and therefore may significantly delay patient evaluation if relied on.

Currently, the diagnosis of hollow viscus injury secondary to blunt trauma remains one of the most diagnostically challenging undertakings in trauma surgery and emergency medicine. The accuracy and reliability of diagnosis is lowered by confounders such as large body habitus, the need for repeated evaluations by the same examiner, concomitant neurologic injury, or altered mental status (Fakhry et al., 2000; Malhotra et al., 2000). Additionally, computed tomography, the gold-standard method of diagnosis of solid visceral injury, can have a false-negative rate of as high as 12% (Malhotra et al., 2000). As it has been shown that a delay of as little as 8 hours can significantly increase mortality in hollow viscus injury, these faults can have serious implications (Fakhry et al., 2000). As Fakhry and colleagues concluded in 1999, "investigation into an efficient method for the timely diagnosis of small bowel injury is urgently needed." To date, this need has not been addressed satisfactorily.

Procalcitonin (PCT) is an acute-phase reactant that has been well-studied in recent years, and is gaining significant traction as a biomarker of sepsis in ICU settings, particularly due to its more rapid rise in serum levels when compared to CRP. PCT is primarily produced in the lungs and intestine, is not metabolized in serum, and avoids hepatic first-pass metabolism. In both human and animal studies, PCT has been shown to be an early marker of bowel necrosis and acute mesenteric ischemia, rising to significantly-detectable levels after only 1 hour (Karabulut et al., 2011; Markogiannakis et al., 2011).

Complement component 5 is a serum protein which is cleaved during activation into two subunits, C5a and C5b, which is the last enzymatic step prior to formation of the membrane attack complex (Mak & Saunders, 2006). Plasma levels of the C5a subunit have been shown to be increased following hemorrhagic shock in swine (Szebeni et al., 2003). Human studies are unfortunately limited, a recent study performed in trauma patients demonstrated that patients with elevated serum C5b levels had both a statistically-significant increase in blood transfusion requirements, development of ARDS and AKI, and mortality (Ganter et al., 2007).

Fibrin-degradation products (FDPs) are among the most well-studied compounds related to the pathophysiology of coagulation, and have been shown to play an important role both prediction of injury severity and diagnosis of fibrinolysis (Kashuk et al., 2010). With regard to hemorrhage, FDPs have been shown to also be one of the most sensitive indicators of the need for massive transfusion and mortality (Hagiwara et al., 2013; Sawamura et al., 2009).

Protein C is a protein that has well-established anticoagulant properties. In a trauma setting, it has been suggested that activated Protein C (aPC) also stimulates tPA release from endothelium, activating plasminogen and initiating fibrinolysis (Kashuk et al., 2010). This primary fibrinolysis may cause the dreaded systemic coagulopathy of trauma, which has been shown lead to as much as a 6-fold increase in mortality (Brohi et al., 2007). Low levels of serum Protein C, which may reflect activation to aPC, have also been associated with prolonged respiratory failure and AKI (Brohi et al., 2007).

Methods & Assays

In one embodiment, the invention provides a method for diagnosing trauma. In one embodiment, the invention provides a method for diagnosing organ-specific trauma or area-specific trauma. In one embodiment, the invention provides a method for prediction of multiple organ dysfunction based on traumatic organ injury score. In one embodiment, the invention provides a method for detecting trauma biomarkers in a biological sample.

In one embodiment, the invention provides a method for diagnosing abdomino-pelvic injury. In one embodiment, the method comprises diagnosing active arterial bleeding, especially from injured abdominal viscera (i.e. spleen and liver, intestinal mesentery, kidneys) and pelvic fractures (i.e. branches off left or right internal iliac arteries).

In one embodiment, the invention provides a method for prognosis in polytrauma. In one embodiment, the invention provides a method for diagnosing the severity of a trauma. In one embodiment, the biomarker panel correlates with injury severity following trauma will allow for immediate prognostication.

In one embodiment, the method discriminates polytrauma with calibration to injury severity following trauma to allow for expedited diagnosis. In one embodiment, the biomarker panel levels correlate with the severity of organ specific trauma and its duration.

In one embodiment, the invention provides a method of risk-stratification. For example, in one embodiment, the invention provides a method of decision-making of severity of bleeding during the most critical time period to detect active hemorrhage in the immediate post-injury setting. In one embodiment, the method comprises selecting the acute management when the biomarker panel levels indicate a risk-stratification so that hemorrhage control may be achieved timely via endovascular or operative techniques). Biomarker panel levels correlate with the severity of hemorrhage and its duration.

In one embodiment, the method comprises: a) obtaining a biological sample from a patient; and b) testing said sample to determine the level of one or more trauma biomarkers; wherein said testing is conducted on an array of agarose beads, conjugated to bioaffinity ligands specific for trauma biomarkers, and wherein signal from said array of agarose beads is analyzed by circular area of interest or line profiling or both.

In certain embodiments, the method comprises detecting the level of at least one, at least two, at least three, at least four, at least five, at least six, at least seven, at least eight, at least nine, at least ten, at least eleven, at least twelve, or at least thirteen, of the biomarkers described herein.

In certain embodiments, the method comprises detecting the level of at least one, at least two, at least three, at least four, at least five, at least six, at least seven, at least eight, at least nine, at least ten, at least eleven, at least twelve, or at least thirteen of the biomarkers of: CRP, myoglobin, NGAL, Cystatin-C, KIM-1, HMGB-1, L-FABP, I-FABP, procalcitonin, properdin, complement component 5, FDP, and protein C.

In one embodiment, the method further comprises assigning a risk-stratification to the patient when the one or more biomarkers is above baseline level. In one embodiment, the baseline level is level of the one or more biomarkers in a sample from a non-injured patient. In one embodiment, baseline level is a standard level of the one or more biomarkers. In one embodiment, the risk-stratification is a high, medium, or low. In one embodiment, the risk-stratification is a numerical score from 0-10. In one embodiment, the risk-stratification is a numerical score from 0-100. In one embodiment, the risk-stratification correlates to the risk of trauma.

In one embodiment, the method further comprises performing an optimal clinical intervention. In one embodiment, the optimal clinical intervention is performed when the level of the one or more biomarkers are above a threshold level. In one embodiment, the optimal clinical intervention is selected from the group consisting of exploratory laparotomy, emergency thoracotomy, resuscitation and chest wall stabilization.

In one embodiment, the biomarker is selected from CRP, myoglobin, NGAL, Cystatin-C, KIM-1, HMGB-1, L-FABP, I-FABP, procalcitonin, properdin, complement component 5, FDP, and protein C.

Biological samples can also be obtained from other sources known in the art, including whole blood, serum, plasma, urine, interstitial fluid, peritoneal fluid, cervical swab, tears, saliva, buccal swab, skin, cerebrospinal fluid, or other tissues including, for example, brain tissues. In one embodiment, the biological sample is blood, saliva, plasma or urine.

In one embodiment, the quantitative results generated will be utilized to train machine learning algorithms to provide an intuitive Trauma ScoreCard.

In one embodiment, a method for training a machine learning algorithm comprises the steps of obtaining a quantity of biological samples from a plurality of subjects, including but not limited to whole blood, serum, plasma, urine, interstitial fluid, peritoneal fluid, cervical swab, tears, saliva, buccal swab, skin, cerebrospinal fluid, or other tissues including, for example, brain tissues, obtaining or calculating one or more biomarkers from the plurality of subjects, including but not limited to CRP, myoglobin, NGAL, Cystatin-C, KIM-1, HMGB-1, L-FABP, I-FABP, procalcitonin, properdin, complement component 5, FDP, and protein C, obtaining one or more trauma characteristics or outcomes from the plurality of subjects, and training a machine learning algorithm to optimize one or more predictive weighting coefficients of the biomarkers in order to build a predictive model. In certain aspects, the method further comprises obtaining a set of demographic data or other characteristics from the plurality of subjects and training the machine learning algorithm to optimize one or more predictive weighting coefficients of the biomarkers and/or demographic data in order to build a predictive model.

Currently, the ability to detect active hemorrhage early in the presentation of an injured patient is currently dependent on hemodynamic parameters, which generally are depressed when bleeding is significant; for example, hypotension may not be seen until 30% of blood volume is lost. The addition of a POC trauma diagnostic panel will assist in decision-making during the most critical time period, i.e. at the time of arrival.

In one embodiment, the diagnostic or biomarker panel is a group of two or more, three or more, four or more, five or more, six or more, seven or more, 8 or more, 9 or more, 10 or more, 11 or more, 12 or more or 13 or more biomarkers. In one embodiment, the diagnostic or biomarker panel provides correlate with the presence and/or severity of trauma and its duration. In one embodiment, there is trauma when each of the biomarkers in the biomarker panel is increased. In one embodiment, there is trauma when each of the biomarkers in the biomarker panel is decreased. In one embodiment, there is trauma when some of the biomarkers in the biomarker panel are decreased and some of the biomarkers in the biomarker panel are increased. In one embodiment, there is trauma when the biomarkers in the biomarker panel are at specific ratios.

In some embodiments, the method further comprises performing an interventional radiologic or operative technique. Exemplary interventional imaging modalities include, but are not limited to fluoroscopy, CT, ultrasound, and MRI. Although fluoroscopy and CT use ionizing radiation, both methods are fast and geometrically accurate. Ultrasound suffers from image quality and tissue contrast problems, but it is fast and inexpensive. MRI provides superior tissue contrast. Exemplary interventional procedures and treatments include, but are not limited to, angiography, angioplasty/stent, chemoembolization, embolization, thrombolysis, biopsy, laparotomy, blood transfusion, RF ablation, cryoablation, and IVC filter.

For example, physicians in the emergency department often base their decisions for a laparotomy combined with biochemical abnormalities. Exemplary biochemical parameters include, but are not limited to, high concentrations of C-reactive protein (CRP) or lactate concentrations. In one embodiment, the physician performs an exploratory laparotomy when biomarker levels of CRP and above 600 µg/ml. In one embodiment, the CRP normal baseline levels are 7.5-8.5 µg/ml. In one embodiment, the physician performs an emergency thoracotomy in an elderly patient (average 72.5±6.4 years) when biomarker levels of CRP are above 1000 µg/ml. In one embodiment In one embodiment, these markers may be used in clinical settings to establish a diagnosis by means of interventions in the emergency department. In one embodiment, these methods provide more extensive diagnostic examinations. In one embodiment, these methods reduce unnecessary invasive interventions (e.g. laparotomy). In one embodiment, these methods allow accurate results to be available to the clinician with short turnaround time. In one embodiment, these methods allow for risk stratification as well as monitoring and targeting therapy.

Assays & Kits

In one aspect, the invention provides an assay for determining the level of a trauma biomarker. In one aspect, the invention provides an assay for diagnosing trauma or the severity of a trauma. In one embodiment, the assay comprises: a microfluidic lab-on-chip based immunoassay that comprises a disposable cartridge and a separate reader, wherein said cartridge fits into a slot on said reader, and said reader performs said immunoassay and outputs a result, wherein the cartridge comprises i) a generally flat substrate having embedded microfluidic channels connecting an inlet port to an embedded downstream assay chamber having a transparent cover and containing a removable array of bead sensors; ii) one or more reagent chambers fluidly connected to and upstream of said assay chamber; and iii) one or more waste fluid chambers fluidly connected to and downstream of said assay chamber; iv) wherein each bead sensor is a porous polymeric bead of size between 50-300 µm±10% having an antibody conjugated thereto, wherein said antibody specific to a biomarker. In one embodiment, wherein the immunoassay has a lower limit of detection for each of said biomarkers of <50 ng/ml and a detection range of at least four orders of magnitude. In one embodiment, cartridge comprises 2 or more, 3 or more, 4 or more, 5 or more, 6 or more, 7 or more, 8 or more, 9 or more, 10 or more, 11 or more or 12 or more of the antibodies.

In one embodiment, the invention provides a kit for diagnosing a trauma. In one embodiment, the kit comprises a cartridge of the invention. In one embodiment, the cartridge is wrapped in an airtight package. In one embodiment, the kit further comprises a vial of assay fluid. The kit can include other components, e.g., instructions for use.

In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C#, Objective-C, Java, JavaScript, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G or 4G/LTE networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

Additional information regarding certain aspects of the system, method, or device described herein, can be found in U.S. Pat. No. 8,257,967, WO03090605, US20060073585, US20060079000, US20060234209, WO2004009840, WO2004072097, U.S. Pat. Nos. 7,781,226, 8,101,431, 8,105,849, US20060257854, US20060257941, US20060257991, WO2005083423, WO2005085796, WO2005085854, WO2005085855, WO2005090983, U.S. Pat. No. 8,377,398, WO2007053186, US20100291431, WO2007002480, US20080050830, WO2007134191, US20080038738, WO2007134189, US20080176253, US20080300798, WO2008131039, US20120208715, WO2011022628, US20130130933, WO2012021714, US20130295580, WO2012065117, US20130274136, WO2012065025, WO2012154306, US20120322682, US20130295580, US20140235487, US20140094391, US20150111778, each of which are incorporated by reference in their entireties.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: The Effect of a Chip-Based Biomarker Analyzer on Early Diagnosis of Occult Injury in Trauma Patients As described herein, a target sample size of 80 patients who present to the emergency department after sustaining traumatic injuries significant enough to warrant "activation" of the trauma surgery team are be evaluated. An aliquot of blood is drawn and analyzed for the presence of specific biomarkers to which the treating team and physicians are blinded. Patients are treated according to usual practice; participation in the study has no effect on patient care aside from this single initial blood draw. Patients' charts are reviewed to determine the presence or absence of abdomino-pelvic injuries, active arterial hemorrhage, or significant polytrauma. This study investigates a biomarker panel for use at the point of care that (1) is sensitive and abdominal organ-specific following trauma, (2) is sensitive and specific for active arterial hemorrhage following abdomino-pelvic injury, and (3) correlates with severity of injury and prognosis in polytrauma.

The p-BNC analyzer and Trauma ScoreCard is a chip-based technology that allows for the rapid identification of the presence of specified biomarkers in a small aliquot of serum. Upon arrival to the emergency department's critical resuscitation unit, a 1-mL sample of serum is drawn from a patient, in addition to the standard set of labs typically drawn during a trauma resuscitation. This sample is then analyzed by the p-BNC system and evaluated for the presence of up to 12 pre-defined biomarkers. Aside from this initial serum draw, patient care is not affected, nor is the treating team informed of the results of the biomarker analysis.

The present invention allows for improved clinical practice by providing the treating clinicians the ability to identify and distinguish those patients with mild/moderate injury with those patients who have sustained severe/critical injuries on arrival. This also allows caregivers to triage patients most effectively in mass casualty situations. The ability to determine injury severity early and to determine who is 'critically injured' is important in the acute period following injury (where complex decision-making is vital) as prognostic variables, including LOS in the hospital or intensive care unit, likelihood of development of complications, and mortality, help guide family decision-making.

With regard to specific organ systems or pathologies, the data presented herein demonstrates detecting injuries to solid organs and/or predicting pathologies which often present diagnostic or therapeutic challenges to trauma surgeons. This is especially true in those patients who present to the emergency department after sustaining blunt trauma, as currently, only 12% of patients without intra-abdominal injuries are able to be identified without computed tomography (Poletti et al., 2004). In total, 12 potential biomarkers were identified for study: CRP, myoglobin, Cystatin-C, NGAL, KIM-1, HMGB-1, L-FABP, I-FABP, procalcitonin, properdin, complement component 5, FDP, and protein C.

To help overcome these significant barriers, a platform to digitize biomarker signatures was designed. These powerful chip-based sensors combine unique biochemical-sensing capabilities with powerful machine learning algorithms, thereby yielding intuitive single-valued indices for assessing trauma (FIG. 1). These tests have the potential to radically reduce costs, decrease wait times, and add new options for patients in need of regular health monitoring. Moreover, these chip-based sensors can be made even more impactful when delivered through mobile health technology able to standardize, store, and serve the growing body of data they create. By adopting lessons from advances in consumer electronics, big data analytics, and web-aware sensors, cloud-connected diagnostics can be made into powerful assets for wellness tracking and behavior modification. In translating information from disease markers into "actionable data", such technology can empower individuals to identify trends and modify their health decisions intelligently.

This study targets the novel application of the chip-based sensor ensemble for multiplexed, quantitative screening of trauma-related biomarker panels at the point of care, as a transformative tool for the diagnosis and management of trauma patients. The biomarkers: CRP, MYO, Protein C, N-GAL, Cystatin-C, HMGB-1, L-FABP, I-FABP, Procalcitonin, Complement 5, D-Dimer, and Properdin are adapted for the first time to this platform. The quantitative results generated are utilized to train machine learning algorithms to provide an intuitive Trauma ScoreCard that may be utilized by healthcare practitioners. The sensor module involves a single-use, credit card sized plastic cartridge employing a sample input port, microfluidics module, reagent blisters, biomarker array, waste reservoir, and high specificity antibody reagents.

Validated biomarker panels that combine information about injury and prognosis will improve clinical decision-making from stratification of patients to therapeutic strategies. An effective mechanical injury biomarker panel will have implications for urban and rural civilian trauma care and ultimately may move into military and global settings.

The programmable bio-nano-chip (p-BNC) platform is developed for screening of trauma-related biomarker panels. Nano-materials and microelectronics have been combined and adapted for the practical implementation of two classes of mini-sensors (bead-based sensors for soluble chemistries) that read out with high-performance yet affordable imaging systems now in development, testing, and clinical validation. Collectively, the two p-BNC sensor ensembles form a modular platform system that demonstrates one of the largest analyte diversity available to date (Christodoulides et al., 2002; Floriano et al., 2009; Goodey et al., 2001; Jokerst et al., 2010; Lavigne et al., 1998; Weigum et al., 2010).

A key feature differentiates the p-BNC platform from other analytical schemata. Unlike typical microfluidic paradigms, in which a single 'chip' is created specific to a type of cell/protein/oligo, this technology is able to measure a broad portfolio of analytes within the same compact system. Likewise, it is possible to create targeted panels by reagent packages, bead capture elements and size-tuned cell collection including modular ensembles. Another important distinction is the different mechanism of analyte capture. While most microfluidic approaches employ planar arrays, the p-BNC approach uses high surface area 3D beads that efficiently concentrate various analytes from biofluids. The technology displays results in minutes, which makes them available at the point of care. Both systems reprogram quickly as new information related to disease signatures is obtained from research settings.

Perhaps the most important feature of the p-BNC platform is its' high-fidelity multiplexing capacity, that is detection of multiple analytes simultaneously. The technology's single format chip-based assay platform allows for a high degree of multiplexing that is unique today, without compromising performance or sensitivity for low concentration analytes, across a broad range of pathophysiology. Likewise, the p-BNC platform exhibits wide assay range capabilities, with excellent limits of detection and quantitation, strong assay reproducibility and most importantly a degree of multiplexing that allows for 8 or more biomarkers to be measured simultaneously. One sample draw and a single assay run on one p-BNC system can provide enough information on levels of multiple biomarkers in the sample and to establish the risk score. More traditional approaches would require multiple blood draws and use a plurality of instruments.

This study evaluates the feasibility of a chip-based biomarker panel for use at the point of care that is both sensitive and specific for abdominal organ injury secondary to trauma. Biomarkers for injured abdominal viscera, specifically the spleen, liver, intestines, and kidneys, whose early assessment following trauma affect diagnostic imaging strategies and medical treatments. Optimized trauma diagnostic panels acquired in the immediate post-injury acute hospital setting improve clinical practice by limiting the use of standard computed tomography (CT) imaging modalities. CT is currently the standard for the diagnosis of abdominal visceral injuries, but it is a costly modality with significant radiation exposure. The comprehensive 12-biomarker panel is assessed via receiver operating curve analyses for its ability to diagnose or exclude organ injuries, including to the spleen, liver, intestines, and kidneys. A scoring system is developed to assess clinical applicability as a pre-test probability score to compare with CT.

This study investigates a biomarker panel for use at the point of care that correlates with severity of injury and prognosis in polytrauma. The identification and development of a biomarker panel that correlates with injury severity following trauma will allow for immediate prognostication. One of the limitations of the Injury Severity Score (ISS) is that it can only be determined after diagnostic imaging studies are completed and interpreted. Optimized trauma diagnostic panels such as the one herein envisioned will improve clinical practice by providing the treating clinicians the ability to identify and distinguish severely injured patients. ROC analysis is performed to determine the diagnostic value of the pre-test probability score for detecting (efficacy of predicting) severity of injury and is tested against ISS.

A single group of patients with a target sample size of 80 who present to the emergency department after sustaining traumatic injuries significant enough to warrant "activation" of the trauma surgery team are evaluated. An aliquot of serum is drawn and analyzed for the presence of 12 specific biomarkers to which the treating team and physicians are blinded. Patients are treated according to usual practice; participation in the study will have no effect on patient care aside from this single initial blood draw. Patients' charts are reviewed to determine the presence or absence of abdomino-pelvic injuries, active arterial hemorrhage, or significant polytrauma. Statistical analysis is performed to determine correlation between injury presence and biomarker levels detected in drawn serum samples as detected by the p-BNC and Trauma ScoreCard analyzer system.

Preclinical Data

The precision study of the agarose beads is important to demonstrate their reproducibility and repeatability. Precision study is an analytical method that describes the closeness of individual measures of an analyte when the procedure is applied repeatedly to multiple aliquots of a single homogenous volume of biological matrix. The precision of an immunoassay is important because it enables an assessment to be made of the probability that a given concentration differs from a specified value. It also describes the repeatability of the test. An immunoassay's repeatability is usually measured as its imprecision and often expressed as the percent coefficient of variation. (% CV) at a particular analyte level as shown below: % CV=100×standard deviation of replicate test values mean of replicate test values. The within-run precision is defined as the precision of the same sample run on several occasions within the same assay. This is also known as intra-assay variation. Between-run precision is a measure of the assay to reproduce the same result on the same sample from run to run and from day to day. It is also known as the inter-assay variation.

Figure 2:
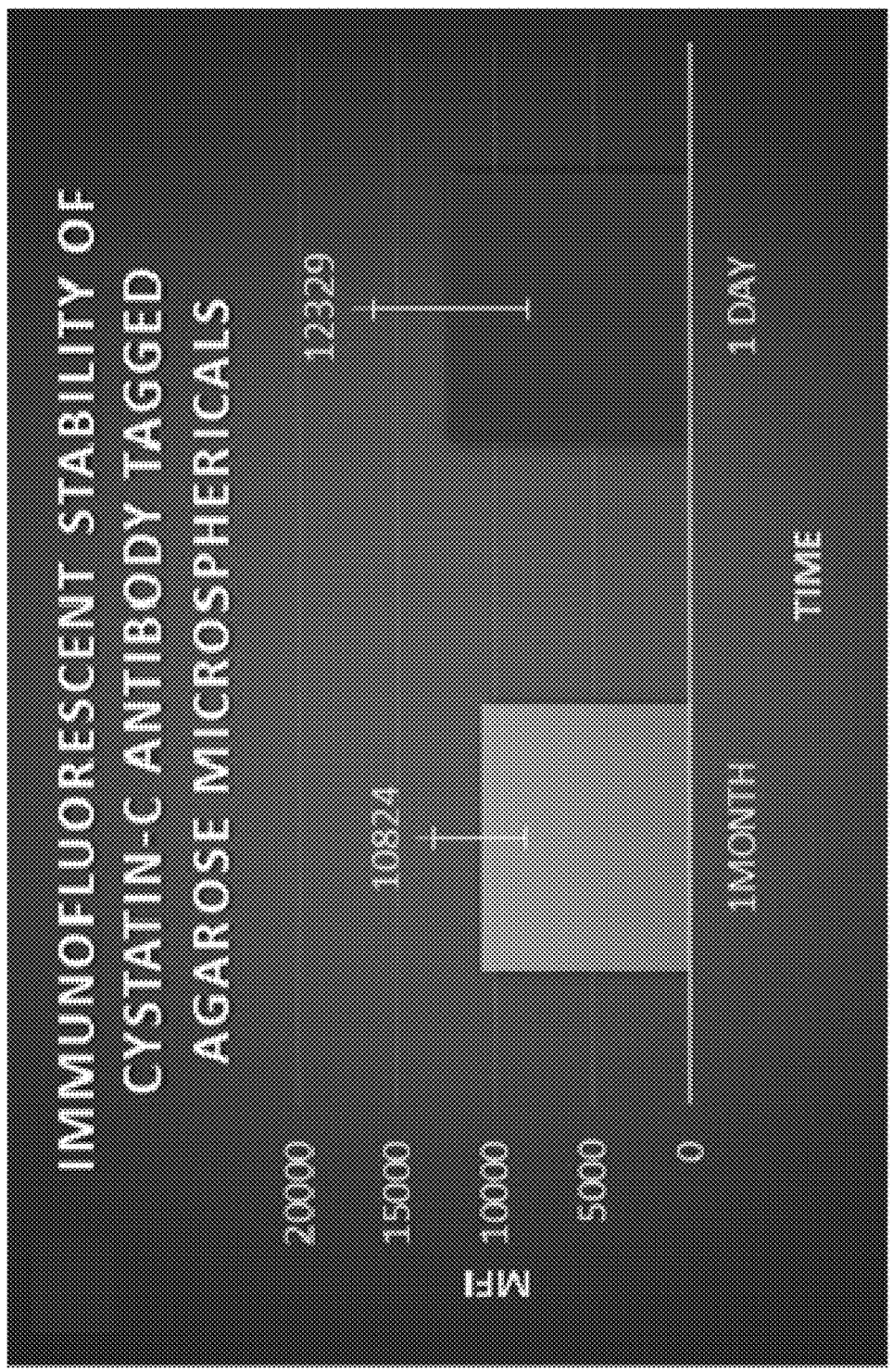
FIG. 2 depicts experimental results demonstrating that mean fluorescence intensity of antibody attached agarose beads were stable and antibodies were not degraded after one month.

The chemical stability of an agarose beads after conjugation with antibody in a given matrix under specific conditions for given time intervals at intended storage temperatures. A study was performed examining storage condition and antibody performance in p-BNC. The assays were repeated 6 times for each case. 2% w/w agarose beads were functionalized with 0.01M glycidol and 0.2M sodium periodate and conjugated with 1 mg/ml cystatin-C (in 0.5 mg). Agarose beads were loaded in bead array in p-BNCs and the cartridge was kept for one month at 4 C°. And functionalized agarose beads freshly conjugated with 1 mg/ml Cystatin-C (in 0.5 mg) and p-BNC bead array was loaded with agarose beads and ran the assay at the same day. 0.8 ug/ml cystatin-C antigen was freshly prepared in cystatin-C human free serum. In FIG. 2, the results indicate that mean fluorescence intensity of antibody attached agarose beads were stable and antibodies were not degraded after one month, the cystatin-C antibody that freshly conjugated on agarose beads have higher mean fluorescence intensity than cystatin-C tagged agarose beads that stored at 4 C° for 1 month, although there were no major difference. Storing these antibodies tagged agarose beads at 4° C. for 1 month does not impact their activity.

Fluorescence intensity of recorded signals with p-BNC device can indicate antigen concentrations. The development of an immunoassay is demonstrated with the assay's ability to accurately identify and quantify the presence of a specified analyte;

In doing so, samples of known analyte concentration are tested according to an optimized procedure and a calibration curve (or dose-response curve) is usually plotted of the signal response as a function of the analyte concentration. The concentration of analyte in the unknown sample may then be interpolated from the calibration curve. An assay's performance can be gauged on its ability to accurately detect: (1) low concentrations of analyte, (2) a wide range of analyte concentrations based on the linearity of the calibration curve or (3) high concentrations of analyte without the calibration curve becoming saturated. Furthermore, the major determining factors of detection threshold are the level and imprecision of the nonspecific binding and error in measurement of the signal and not necessary the antibody's equilibrium constant.

Thus, an assay with a low detection threshold will 1) be optimized with high concentrations of antibody in relation to the antigen, 2) have low non-specific binding of the detecting antibody, and 3) have a signal generator with high activity.

The log plot has the advantage of having a linear region at concentrations where the capture antibody is not saturated with analyte. The complexity of curve fitting is greatly reduced if this plot is used and if the analysis is restricted to non-saturated regions. Such data is more reliable and can be readily fitted by a least-squares analysis. Recovery of an analyte in an assay is the detector response from an amount of the analyte added to and extracted from the biomarkers compared to the detector response obtained for the true concentration of the standard. Recovery of the analyte need not to be 100% but the extent of recovery of an analyte and internal standard should be consistent, precise and reproducible. However, the wide variety of assay designs dictates that optimal assay conditions and reagent concentrations must be experimentally determined to provide the desired analytical information.

Increasing the amount of detecting antibody, however, also increases the amount of its non-specific binding (and its associated error). Eventually a point is reached where the level of nonspecific binding increases faster that the rate of specific binding and the S/N begins to drop. Thus, a balance must be found in the optimization procedure so that the highest signal is attained with the lowest level of non-specific binding. The log plot has the advantage of having a linear region at concentrations where the capture antibody is not saturated with analyte. The complexity of curve fitting is greatly reduced if this plot is used and if the analysis is restricted to non-saturated regions. Such data is more reliable and can be readily fitted by a least-squares analysis. When calibrating the system, four or five parameter logistic curves are used for the standard to fit recorded data points; the concentration-response relationship is most often fitted to a 4-parameter logistic model, although others may be used with suitable validation.

The use of anchoring points in the asymptotic high- and low-concentration ends of the standard curve may improve the overall curve fit.

The best optimal conditions with 0.5M glycidol and 0.2M sodium periodate for activation were repeated for 4% agarose beads for Cystatin-C biomarker (1 mg/ml in 0.5 mg).

Figure 3:
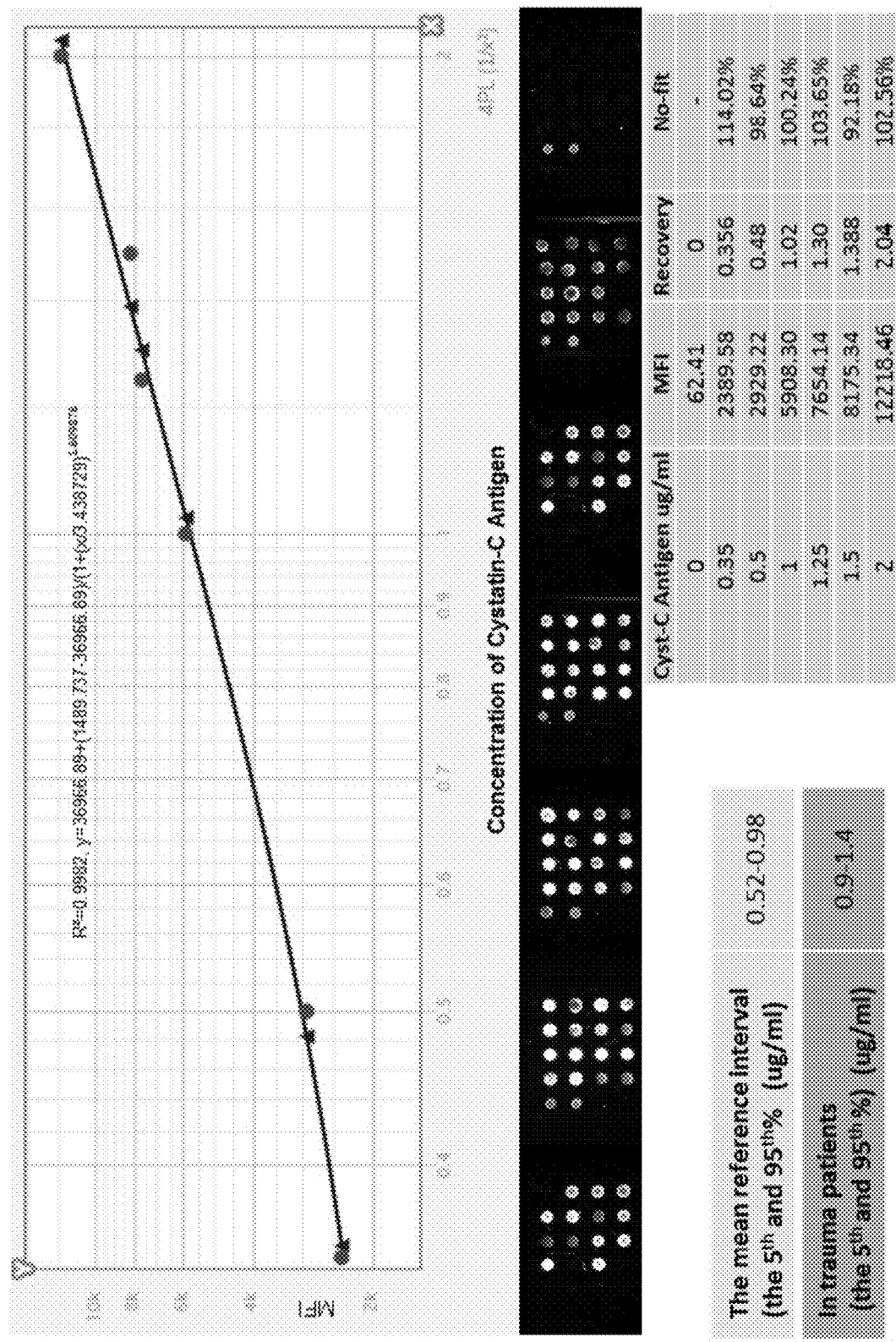
FIG. 3 depicts experimental results demonstrating the Cystatin-C antigen standard curve.

In FIG. 3, seven different concentrations; 0, 0.35, 0.5, 1, 1.25 and 1.5 and 2 ug/ml of Cystatin-C antigen were determined to create a standard curve based on trauma serum sample reference from literature survey. The mean reference interval of Cystatin-C protein in non-trauma cases are between 0.52 and 0.98 ng/ml (the $5^{th}$ and $95^{th}$%). In trauma case, Cystatin-C values are elevated in serum samples the range of 0.9 to 1.4 µg/ml. The mean recovery was found 114.02, 98.64, 100.24, 103.65, 92.18, and 102.56%, respectively. The dose response for cystatin-C shows an adequate fit to the 4-parameter logistic curve ($R^2$=0.9982).

Preclinical data in use of p-BNC technologies resulted in improvement of the analysis performance by increasing the sensitivity, decreasing the analysis time, simplification of the assay procedure, automation of the method, and miniaturization of the analytical equipment ScoreCard Analysis The multiplexing capacity of the technology is important for all aspects of care related, including diagnosis, prognosis, monitoring, risk stratification and guidance for therapeutic interventions of patients. As such, these dedicated efforts in a single setting results in the creation of a new diagnostic trauma risk assessment tool based on a multiplexed panel of biomarkers, the ScoreCard, described in the following section.

Clinical decision support systems (CDSSs) are support tools which assist in medical decision-making by providing clinicians with personalized assessments or recommendations and offer a promising solution for managing and diagnosing trauma, diseases, and disorders. CDSSs have been developed, featuring various machine-learning methods such as artificial neural networks, Support Vector Machines, random forest, Bayesian networks, logistic regression, and ensemble methods. Although CDSSs promise enhanced diagnostic results, shorter wait times, and reduced cost versus the standard of care, physicians may be hesitant to implement "black box" CDSSs (i.e., the algorithm's results and methods to obtain them are either uninterpretable or not capable of providing actionable therapeutic recommendations). Therefore, the ScoreCard uses a lasso logistic regression approach, converting risk factors and biomarker data into a single score with interpretable and clinically useful information in the form of logistic regression coefficients.

The ScoreCard assay comprises a multiplex panel of biomarkers from a diverse pathophysiology. This multi-marker approach with a patho-biologically diverse panel of biomarkers has been demonstrated to improve performance in risk prediction. In addition, a selection of markers that are differentially expressed across various traumas provides new opportunities for trauma prediction models. Further, it is important to train the models with predictors that are uncorrelated. When biomarkers from the same pathophysiology are selected for a model, the predictors tend to be highly correlated. Conversely, selecting biomarkers from a diverse background are expected to increase the overall information content in the predictive model. In addition to the Trauma scorecard, the related area of Cardiac ScoreCard has also been developed. In some cases, complications with cardiac function occur as a result of severe trauma injury and as such inclusion of the cardiac scorecard is relevant to this discussion.

A predictive model for assessing overall heart health for consumer wellness testing was recently developed. Briefly, the wellness ScoreCard model (AUC=0.84) outperformed both the Framingham 10-year CVD risk score (AUC=0.79) and a biomarker-only model (AUC=0.77) in terms of discrimination between high risk and low risk patient groups. Additionally, the ScoreCard model shows good calibration across deciles of predicted risk (Hosmer-Lemeshow p=0.98), demonstrating its usefulness as a score for wellness. Multivariate ScoreCard algorithm showed better discrimination in diagnosing than the single-marker score, suggesting that the diagnosis can be enhanced by adding auxiliary biomarkers and patient demographics.

One advantageous feature of lasso logistic regression is automatic feature selection. Feature selection reduces model complexity and improves generalization by discarding unnecessary predictors while retaining the most relevant, and the lasso logistic regression method performs this feature selection by shrinking the regression coefficients. Not only does this feature selection approach improve prediction performance, but it also provides stakeholders with a prioritized list of biomarker candidates for future implementation in multi-marker panels. In the wellness model, the lasso method selected 15 predictors (i.e., nonzero coefficients) with BMI (βBMI=0.82), smoking (βSmoking=0.47), age (βAge=0.45), myoglobin (βMYO=0.34), gender (βGender=0.19), and IL-113 (βIL-1β=0.17) having the largest effect sizes. These results suggest that the discrimination between high and low risk patients is contingent on a relatively large number of predictors, comprising demographics and biomarkers from a diverse pathophysiology. On the other hand, the lasso method returned a sparse model for diagnosis with only four non-zero predictors: BNP (βBNP=1.51), cTnI (I3cTnI=0.28), BMI (βBMI=0.25), and age (βAge=0.06). From a practical assay development perspective, this sparse model, made possible through lasso-based feature selection methods, has the potential to significantly reduce the cost of reagents and simplify the assay chemistry.

Primary Endpoint

The primary endpoint of this pilot study is the correlation between injury presence, confirmed clinically or radiographically, and levels of serum biomarkers detected in blood samples obtained from patients presenting to the ED after acute traumatic injury. The purpose of this endpoint is to demonstrate that abdominal organ-specific biomarkers can discriminate an abdominal AIS≥3. The goal is to show that biomarkers can rule-out solid visceral injury and reduce unnecessary abdominal CT.

Statistical analyses: Discrimination performance for each biomarker of severe abdominal injury is measured via sensitivity, specificity, PPV, NPV, and ROC curve analysis using a one-sided test of significance with p=0.05.

The required sample size for comparison of area under a ROC curve with a null hypothesis value was determined using methods from Hanley and McNeil (Hanley & McNeil, 1982). The assumptions are a 1:1 ratio of cases/non-cases, a Type I error 0.05 (α, Significance), Type II error 0.10 (β, 1-Power), and a null hypothesis AUC value 0.5 (i.e., no discriminating power). The hypothesized AUC values were derived from Table 1 for each biomarker. Table 1 shows the estimated number of cases and non-cases needed to show that each biomarker assay's discrimination performance is significant from the null hypothesis. For this aim, the target subject sample size is the maximum number of cases/non-cases required for any biomarker assay (CRP). Thus, a minimum of 37 cases and 37 non-cases are required to satisfy the requirements of this primary endpoint.

TABLE 1

Sample size estimates for abdominal organ-specific biomarker assays

| Biomarker | AUC | Number of Cases | Number of Non-cases | Total |
|---|---|---|---|---|
| CRP | 0.710 | 37 | 37 | 74 |
| Myoglobin | 0.840 | 12 | 12 | 24 |
| NGAL | 0.900 | 8 | 8 | 16 |
| Cystatin-C | 0.880 | 11 | 11 | 22 |

TABLE 1-continued

Sample size estimates for abdominal organ-specific biomarker assays

| Biomarker | AUC | Number of Cases | Number of Non-cases | Total |
|---|---|---|---|---|
| HMGB-1 | 0.830 | 13 | 13 | 26 |
| L-FABP | 0.837 | 12 | 12 | 24 |
| I-FABP | 0.850 | 11 | 11 | 22 |
| Procalcitonin | 0.770 | 21 | 21 | 42 |
| Complement 5 | — | — | — | — |
| D-Dimer | 0.880 | 9 | 9 | 18 |
| Properdin | — | — | — | — |

Secondary Endpoint

The secondary endpoint of this pilot study is demonstrating the utility of a biomarker panel for discriminating abdominal injury. The purpose of this endpoint is to demonstrate that a multivariate model of biomarkers discriminates an abdominal AIS≥3. The primary goal is to show that this multivariate biomarker model can rule-out solid visceral injury and reduce unnecessary abdominal CT and to assess the clinical applicability of the multi-biomarker model response as a pre-test probability score to CT. (Case is Abdominal injuries with AIS≥3; non-case is Healthy control (matched for age, gender, etc.)).

Statistical analyses: Discrimination performance for the multi-biomarker logistic regression model of severe abdominal injury is measured via sensitivity, specificity, PPV, NPV, AUC, and ROC curve analysis using a one-sided test of significance with p=0.05. The model training is performed using 5-fold cross-validation, and model testing is performed on a ⅓ holdout set. The sensitivity and specificity of the biomarker panel is compared to CT measurements for the possibility to rule-out solid visceral injury and reduce unnecessary abdominal CT.

Sample size justification: For secondary endpoint 1, the required sample size for comparison of area under a ROC curve with a null hypothesis value was determined using methods from Hanley and McNeil (Hanley & McNeil, 1982). The assumptions are a 1:1 ratio of cases/non-cases, a Type I error 0.05 (α, Significance), Type II error 0.10 (β, 1-Power), and a null hypothesis AUC value 0.5 (i.e., no discriminating power). Table 2 shows the estimated number of cases and non-cases needed to show that each biomarker assay's discrimination performance is significant from the null hypothesis at a range of hypothesized AUC values between 0.6-0.9. A previous study from Mistral et al. found that the clinical judgement of senior trauma leaders for the diagnosis of serious-to-critical injury (AIS≥3) prior to a whole-body CT scan had an AUC of 0.70 (95% CI, 0.64 to 0.75) (Mistral et al., 2017). These results serve as a conservative prior estimate for our hypothesized AUC value of 0.70; therefore, a minimum of 41 cases and 41 non-cases are required for the model training and a minimum of 21 cases and 21 non-cases are required for the ⅓ hold out training set (total of 62 cases and 62 non-cases).

TABLE 2

Sample size estimates for the multi-biomarker model at various projected AUC values

| AUC | Number of Cases | Number of Non-cases | Total |
|---|---|---|---|
| 0.60 | 172 | 172 | 344 |
| 0.65 | 75 | 75 | 150 |
| 0.70 | 41 | 41 | 82 |
| 0.75 | 25 | 25 | 50 |
| 0.80 | 17 | 17 | 34 |
| 0.85 | 11 | 11 | 22 |
| 0.90 | 8 | 8 | 16 |

The secondary endpoint also investigates a biomarker panel for use at the point of care that is sensitive and specific for the detection of active arterial hemorrhage following abdomino-pelvic injury. The purpose of this endpoint is to demonstrate that a multivariate model of biomarkers discriminates active arterial extravasation. The goal is to show that a trauma diagnostic panel with the ability to detect active hemorrhage in the immediate post-injury setting will improve clinical practice by tailoring the acute management so that hemorrhage control may be achieved timely via endovascular or operative techniques. (Case is Active arterial extravasation on CT of abdomen/pelvis; Non-case is Healthy control (matched for age, gender, etc.)).

Statistical analyses: Discrimination performance for the multi-biomarker logistic regression model of active arterial hemorrhage following abdomino-pelvic injury is measured via sensitivity, specificity, PPV, NPV, AUC, ROC curve analysis using a one-sided test of significance with p=0.05. The model training is performed using 5-fold cross-validation, and model testing are performed on a ⅓ holdout set.

Sample size justification: For secondary endpoint 2, the required sample size for comparison of area under a ROC curve with a null hypothesis value was determined using methods from Hanley and McNeil (Hanley & McNeil, 1982). The assumptions are a 1:1 ratio of cases/non-cases, a Type I error 0.05 (α, Significance), Type II error 0.10 (β, 1-Power), and a null hypothesis AUC value 0.5 (i.e., no discriminating power). Table 2 shows the estimated number of cases and non-cases needed to show that the multi-biomarker model discrimination performance is significant from the null hypothesis at a range of hypothesized AUC values between 0.6-0.9. Aoki et al. predicted extravasation in pelvic fractures from coagulation biomarker D-Dimer with an AUC of 0.88 (Aoki et al., 2016). These results serve as a prior estimate for our more conservative hypothesized AUC value of 0.85; therefore, a minimum of 11 cases and 11 non-cases are required for the model training and a minimum of 6 cases and 6 non-cases are required for the ⅓ hold out training set (total of 17 cases and 17 non-cases).

The secondary endpoint also investigates a diagnostic biomarker panel for use at the point of care that correlates with severity of injury in polytrauma. The purpose of this endpoint is to demonstrate that a multivariate model of biomarkers and other relevant risk factors discriminate polytrauma as indicated by ISS>15. One of the limitations of the ISS is that it can only be determined after diagnostic imaging studies are completed and interpreted. Optimized trauma diagnostic panels and predictive models such as the one herein envisioned will discriminate polytrauma with calibration to injury severity following trauma to allow for expedited diagnosis. Statistical analyses: Discrimination performance of multivariate logistic regression in distinguishing severe injury is measured via sensitivity, specificity, PPV, NPV, AUC, and ROC curve analysis using a one-sided test of significance with p=0.05. The model training is performed using 5-fold cross-validation, and model testing is performed on a ⅓ holdout set. Calibration performance is determined by Hosmer-Lemeshow goodness of fit statistic to determine whether the model adequately fits the data. (Case is ISS>14; Non-case is ISS≤15).

Sample size justification: For secondary endpoint 3, the required sample size for comparison of area under a ROC curve with a null hypothesis value was determined using methods from Hanley and McNeil (Hanley & McNeil, 1982). The assumptions are a 1:1 ratio of cases/non-cases, a Type I error 0.05 (α, Significance), Type II error 0.10 (β, 1-Power), and a null hypothesis AUC value 0.5 (i.e., no discriminating power). Table 2 shows the estimated number of cases and non-cases needed to show that each biomarker assay's discrimination performance is significant from the reference AUC at a range of hypothesized AUC values between 0.6-0.9. A previous study from Mistral et al. found that the clinical judgement of senior trauma leaders for the diagnosis of serious-to-critical injury (AIS≥3) prior to a whole-body CT scan had an AUC of 0.70 (95% CI, 0.64 to 0.75) (Mistral et al., 2017). These results serve as a conservative prior estimate for our hypothesized AUC value of 0.70; therefore, a minimum of 41 cases and 41 non-cases are required for the model training and a minimum of 21 cases and 21 non-cases are required for the ⅓ hold out training set (total of 62 cases and 62 non-cases).

Criteria

Table 3 demonstrates the trauma activation Criteria.

and interpretation such as renal failure, liver failure, active malignancy, or sepsis.
3. Known use of medications that can cause hepatotoxicity, nephrotoxicity, or rhabdomyolysis
4. Patients under arrest or convicts under federal or correctional custody
5. HIV and/or HBC virus containing samples Statistical Methods Discrimination performance for each biomarker of severe abdominal injury is measured via sensitivity, specificity, PPV, NPV, and ROC curve analysis using a one-sided test of significance with p=0.05

To obtain preliminary data quantifying the signal-to-noise ratio of concentration changes against the analytic sensitivity of available diagnostic instrumentation. At least three aliquots are drawn from each subject's samples at each time-point for each instrument. These are used to determine sample-to-sample variability for each diagnostic device. Information regarding sample-to-sample variability are used to establish the ratio of concentration changes against analytic sensitivity (signal-to-noise ratio).

To validate the p-BNC technology for trauma score testing at the point-of-care and correlation to laboratory-based methods the p-BNC system are validated via correlation to reference methods. Blood samples are evaluated for all patients at all time-points on the fully automated p-BNC system and compared to results obtained using a gold

TABLE 3

| | |
|---|---|
| Level 1 | Physiologic Criteria:<br>    Impending respiratory failure or intubated<br>    Systolic blood pressure ≤90 mmHg<br>        Systolic blood pressure ≤20 mmHg below age appropriate blood pressure in pediatric patients (age <15 years)<br>    GCS <10<br>    HR >120<br>Other Criteria:<br>    All penetrating injuries to the head, neck, torso, or extremities proximal to the elbows or knees (excluding minor lacerations)<br>    Any penetrating injury with hemodynamic instability<br>    Falls >30 feet (>10 feet or 2 × height in age <15)<br>    Any extremity amputation proximal to the wrist or ankle<br>    Crushed, mangled, degloved, or pulseless extremity<br>    Pelvic fracture (excluding falls from standing)<br>    Two or more long bone fractures<br>    Paraplegia/Quadriplegia<br>    Inhalation injury or $2^{nd}$ and $3^{rd}$ degree burns involving >20% body surface area<br>    Transfers from other hospitals receiving blood<br>    Discretion of Attending Physician or Nursing |
| Level 2 | None of the Above, and Any of the Following:<br>Physiologic Criteria<br>    GCS <13 if not secondary to intoxication<br>Other Criteria:<br>    Patients on anticoagulation therapy with falls and suspected head trauma<br>    Falls >10 feet<br>    Motor vehicle crash with:<br>        Ejection or death of a passenger in same car<br>        Intrusion >12 inches into patient's passenger area<br>    Pregnancy beyond 20 weeks and significant mechanism of injury<br>    >20 mph impact auto-pedestrian, auto-bicycle, motorcycle crash<br>    Any question of spinal cord injury other than paraplegia or quadriplegia<br>    $1^{st}$ and $2^{nd}$ degree burns ≥5% and ≤20% body surface area<br>    Discretion of Attending Physician or Nursing |

Individuals who meets any of the following criteria are excluded from participation in this study:
1. Receive blood transfusion prior to initial trauma lab draw (blood transfusion itself may contribute to the elevation of certain biomarkers)
2. Diagnosis or evidence of clinically relevant and uncontrolled medical illness likely to confound study results standard [Siemens Dimension EXL or Centaur CP] immunoassay system and/or Luminex Assay System. $R^2 > 0.9$ is considered adequate performance.

Measures of central tendency for continuous data include means and standard deviations for Gaussian data, and medians and interquartile ranges for non-Gaussian data. Categorical data are represented by frequencies and percentages. Comparison of data between the two groups will include t-tests for continuous data and chi-square tests for categorical data.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A testing cartridge comprising a generally flat substrate having thereon individual bead sensors arranged in an array, wherein each said bead sensor is an agarose bead having an antibody bound thereto to form a bead sensor, wherein the antibody is specific for a trauma biomarker selected from the group consisting of abdomino-pelvic trauma, organ-specific trauma, hemorrhage, and polytrauma; and wherein the bead sensors include antibodies specific for biomarkers of C-reactive protein (CRP), myoglobin, Neutrophil Gelatinase-associated Lipocalin (NGAL), Cystatin-C, Kidney Injury Marker 1 (KIM-1), High Mobility Group Box 1 (HMGB-1), Liver Fatty Acid Binding Protein (L-FABP), Intestinal Fatty Acid Binding Protein (I-FABP), procalcitonin, properdin, complement component 5, Fibrin Degradation Products (FDP), and protein C.

2. The testing cartridge of claim 1, further comprising internal microfluidics on said substrate for carrying fluid to and from said bead sensors.

3. The testing cartridge of claim 2, further comprising a sample entry port.

4. The testing cartridge of claim 3, further comprising at least one reagent blister fluidly connected to said bead sensors.

5. The testing cartridge of claim 4, further comprising at least one waste fluid chamber fluidly connected to and downstream of said bead sensors.

6. The testing cartridge of claim 4, further comprising positive and negative control bead sensors and calibrator bead sensors.

7. The testing cartridge of claim 4, wherein every said bead sensor is present in said array in at least duplicate.

8. The testing cartridge of claim 4, wherein said antibody is conjugated to said bead sensor via a linker.

9. The testing cartridge of claim 1, said cartridge further comprising:

a) one or more reagent chambers fluidly connected to and upstream of said array; and b) one or more waste fluid chambers fluidly connected to and downstream of said array;

c) a sample inlet upstream and fluidly connected to said one or more reagent chambers; and d) wherein each bead sensor has a size between 50-300 µm±10%.

10. A trauma diagnostic system comprising:

a microfluidic lab-on-chip based immunoassay that comprises the cartridge of claim 9 and a separate reader, wherein said cartridge fits into a slot on said reader, and said reader performs said immunoassay and outputs a result.

11. An assay for diagnosing a trauma selected from the group consisting of abdomino-pelvic trauma, organ-specific trauma, hemorrhage, and polytrauma, comprising:

obtaining a biological sample from a patient; and immunologically testing said sample to determine the level of trauma biomarkers;

wherein said testing is conducted on an array of agarose beads, conjugated to antibodies, and wherein signal from said array of agarose beads is analyzed by circular area of interest or line profiling or both; and wherein the antibodies include antibodies specific for biomarkers of C-reactive protein (CRP), myoglobin, Neutrophil Gelatinase-associated Lipocalin (NGAL), Cystatin-C, Kidney Injury Marker 1 (KIM-1), High Mobility Group Box 1 (HMGB-1), Liver Fatty Acid Binding Protein (L-FABP), Intestinal Fatty Acid Binding Protein (I-FABP), procalcitonin, properdin, complement component 5, Fibrin Degradation Products (FDP), and protein C.

* * * * *